(12) United States Patent
Saylor et al.

(10) Patent No.: US 7,776,260 B2
(45) Date of Patent: Aug. 17, 2010

(54) APPARATUS AND METHOD FOR THE IRRADIATION OF RADIATION SENSITIVE MATERIALS

(75) Inventors: Michael C. Saylor, Vienna, VA (US); Stephen C. Yeadon, Hampton, NJ (US)

(73) Assignee: Ethicon, Inc., Somerville, NJ (US)

( * ) Notice: Subject to any disclaimer, the term of this patent is extended or adjusted under 35 U.S.C. 154(b) by 726 days.

(21) Appl. No.: 11/608,867

(22) Filed: Dec. 11, 2006

(65) Prior Publication Data

US 2008/0135782 A1    Jun. 12, 2008

(51) Int. Cl.
*A61L 2/08*   (2006.01)

(52) U.S. Cl. .................... 422/22; 165/170; 165/186; 62/530

(58) Field of Classification Search .............. 62/451, 62/530; 165/186
See application file for complete search history.

(56) References Cited

U.S. PATENT DOCUMENTS

| | | | |
|---|---|---|---|
| 4,354,359 A * | 10/1982 | Hall et al. .................. 62/299 |
| 5,103,651 A * | 4/1992 | Coelho et al. .............. 62/341 |
| 5,272,887 A * | 12/1993 | Zendzian, Sr. ............. 62/295 |
| 5,362,442 A | 11/1994 | Kent |
| 5,504,007 A | 4/1996 | Haynes |
| 6,187,572 B1 | 2/2001 | Platz et al. |
| 6,239,048 B1 | 5/2001 | Wilson et al. |
| 6,486,482 B1 | 11/2002 | Anderberg et al. |
| 6,803,227 B2 * | 10/2004 | Wood et al. ............ 435/284.1 |
| 6,908,591 B2 | 6/2005 | MacPhee et al. |
| 6,979,829 B2 * | 12/2005 | Calvert et al. ............ 250/472.1 |
| 2003/0060747 A1 | 3/2003 | Fries et al. |
| 2004/0211916 A1 | 10/2004 | Calvert et al. |

FOREIGN PATENT DOCUMENTS

| | | | |
|---|---|---|---|
| EP | 653215 A1 * | 5/1995 |
| JP | 8075389 | 1/2003 |
| WO | 9831403 | 7/1998 |
| WO | 03/086479 A1 | 10/2003 |
| WO | 2008/008436 A1 | 1/2008 |

OTHER PUBLICATIONS

ISO/ASTM 51649:2005(E)—"Standard Practice For Dosimetry In An Electron Beam Facility For Radiation Processing At Energies Between 300keV and 25 MeV1"; pp. 1-29, 2005.

* cited by examiner

*Primary Examiner*—Elizabeth L McKane
(74) *Attorney, Agent, or Firm*—Roberts Mlotkowski Safran & Cole, P.C.

(57) ABSTRACT

An apparatus for the irradiation of a radiation sensitive material. The apparatus includes at least one thermally conductive tank for containing a heat transfer medium therein, said at least one thermally conductive tank having a first wall and a second wall in a parallel spaced relationship, said second wall having an outer surface for placing a radiation sensitive material thereon. Also disclosed is a system and method of irradiating a radiation sensitive material.

19 Claims, 4 Drawing Sheets

APPARATUS AND METHOD FOR THE IRRADIATION OF RADIATION SENSITIVE MATERIALS

FIELD

This invention relates to biological products and, more particularly, to methods for the sterilization of radiation sensitive materials to reduce the level of active biological contaminants.

BACKGROUND

Various products and materials are routinely irradiated to preserve or modify their characteristics. Among the processes employing irradiation are sterilization of medical devices, disinfection of consumer products, food irradiation for parasite and pathogen control, insect disinfestation and shelf-life extension, control of pathogens and toxins in drinking water, control of pathogens and toxins in liquid or solid waste, modification of characteristics of semiconductor devices, polymerization of monomers, grafting of monomers onto polymers, cross-linking or degradation of polymers, curing of composite materials, color enhancement of gemstones and other materials, and research on radiation effects on materials.

Biological materials that are prepared for human, veterinary, diagnostic and/or experimental use can contain unwanted and potentially dangerous biological contaminants or pathogens, such as viruses, bacteria, in both vegetative and spore states, (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single-cell or multicellular parasites. Consequently, it is of utmost importance that any biological contaminant or pathogen in the biological material be inactivated before the product is used.

Ionizing radiation treatments such as gamma-irradiation, electron beam irradiation, and x-ray irradiation generate free radicals and other activated molecules that damage the biological components of contaminating bacteria, fungi, and viruses and thus ensures their inactivation. However, the biological materials may also be damaged by free radicals and activated molecules, which can harm the integrity of the material. In view of these issues, many new medical advances cannot be implemented because the sterilization industry is unable to provide a suitable procedure as part of the manufacturing process.

Issues involving sterilization exist in other areas of medical treatment as well, such as blood transfusions, blood factor replacement therapy, organ transplants and other forms of human therapy corrected or treated by intravenous, intramuscular or other forms of injection or introduction. Sterilization is also critical for the various biological materials that are prepared in media which contain various types of plasma and/or plasma derivatives or other biologic materials and which may contain harmful prions, bacteria, viruses and other biological contaminants or pathogens.

Irradiation processes are frequently characterized by the minimum absorbed dose required to achieve the desired effect and a maximum dose limit that is set on the basis of what the product can tolerate and still be functional. The dose distribution within a product depends on process load characteristics, irradiation conditions, and operating parameters. The operating parameters include electron energy and beam current, beam dispersion parameters and product material handling, including the control of a product's thermal profile. These parameters are particularly critical when the product is a radiation sensitive material.

U.S. Pat. No. 5,362,442 proposes a method for sterilizing products to remove biological contaminants such as viruses, bacteria, yeasts, molds, mycoplasmas and parasites. The method proposed requires providing the product in a form that contains less than 20% solids and subsequently irradiating the product with gamma irradiation over an extended period of time. The product is irradiated for a period of not less than 10 hours. The extended irradiation time in conjunction with the low level of solids in the product is said to substantially reduce the damage to the product. The method is said to be useful in sterilizing sensitive materials such as blood and blood components.

U.S. Pat. No. 6,187,572 proposes a method for inactivating viral and/or bacterial contamination in blood cellular matter, such as erythrocytes and platelets, or protein fractions. It is proposed that the cells or protein fractions are mixed with chemical sensitizers, frozen or freeze-dried, and irradiated with, for example, UV, visible, gamma or X-ray radiation while in the solid state.

U.S. Pat. No. 6,239,048 proposes a substrate such as a woven or nonwoven fabric bound with a light-activated dye alone or in combination with additional conventional antimicrobial agents. The proposed substrate is impregnated with a light-activated non-leachable dye said to have antimicrobial and/or antiviral characteristics that can be imparted to the substrate. Upon exposure to light, the dye is reported to generate singlet oxygen that is said to kill microorganisms and viruses.

U.S. Pat. No. 6,908,591 proposes methods for sterilizing biological materials to reduce the level of one or more active biological contaminants or pathogens, such as viruses, bacteria, yeasts, molds, fungi, prions or similar agents responsible, for TSEs and/or single or multicellular parasites. The methods proposed involve the use of flavonoid/flavonol stabilizers in sterilizing biological materials with irradiation.

W.O. Publication No. 98/31403 proposes methods of radiation-sterilizing a lyophilized collagen-based biomaterial and compositions of lyophilized collagen-based biomaterials.

Despite these advances in the art, there remains a need for methods of sterilizing radiation sensitive biological materials that are effective for reducing the level of active biological contaminants or pathogens without an adverse effect on the material itself.

SUMMARY

In one aspect, provided is an apparatus for the irradiation of a radiation sensitive material. The apparatus includes at least one thermally conductive tank for containing a heat transfer medium therein, the at least one thermally conductive tank having a first wall and a second wall in a parallel spaced relationship, the second wall having an outer surface for placing a radiation sensitive material thereon.

In another aspect, provided is a system for the irradiation of a radiation sensitive material. The system includes a first thermally conductive tank for containing a heat transfer medium therein, the first thermally conductive tank having a first wall and a second wall in a parallel spaced relationship, the second wall having an outer surface for placing a radiation sensitive material thereon, a second thermally conductive tank for containing a heat transfer medium therein, the second thermally conductive tank having a first wall and a second wall in a parallel spaced relationship, the second wall having an outer surface for contacting the radiation sensitive material and means for securing the second thermally conductive tank to the first thermally conductive tank to form an assembly so that the outer surface of the second wall of the second thermally conductive tank faces the outer surface of the second wall of the at lease one thermally conductive tank when the radiation sensitive material is placed therebetween.

In yet another aspect, provided is a method of irradiating a radiation sensitive material having a first surface and a second surface. The method includes steps of placing the first surface of a radiation sensitive material on a first thermally conductive tank for containing a heat transfer medium therein, the first thermally conductive tank having a first wall and a second wall in a parallel spaced relationship, the second wall having an outer surface for receiving the radiation sensitive material, placing a second thermally conductive tank for containing a heat transfer medium therein upon the second surface of a radiation sensitive material radiation sensitive material, the second thermally conductive tank having a first wall and a second wall in a parallel spaced relationship, the second wall having an outer surface for contacting the radiation sensitive material, securing the second thermally conductive tank to the first thermally conductive tank to form an assembly so that the outer surface of the second wall of the second thermally conductive tank faces the outer surface of the second wall of the at least one thermally conductive tank when the radiation sensitive material is placed therebetween; filling each of the first and the second thermally conductive tanks with a heat transfer medium and irradiating the radiation sensitive material with a suitable radiation at an effective rate and time to sterilize the radiation sensitive material.

BRIEF DESCRIPTION OF THE DRAWINGS

The invention will now be described in more detail with reference to the forms herein disclosed, given only by way of example, and with reference to the accompanying drawings, in which.

DETAILED DESCRIPTION

Definitions

Figure 1:
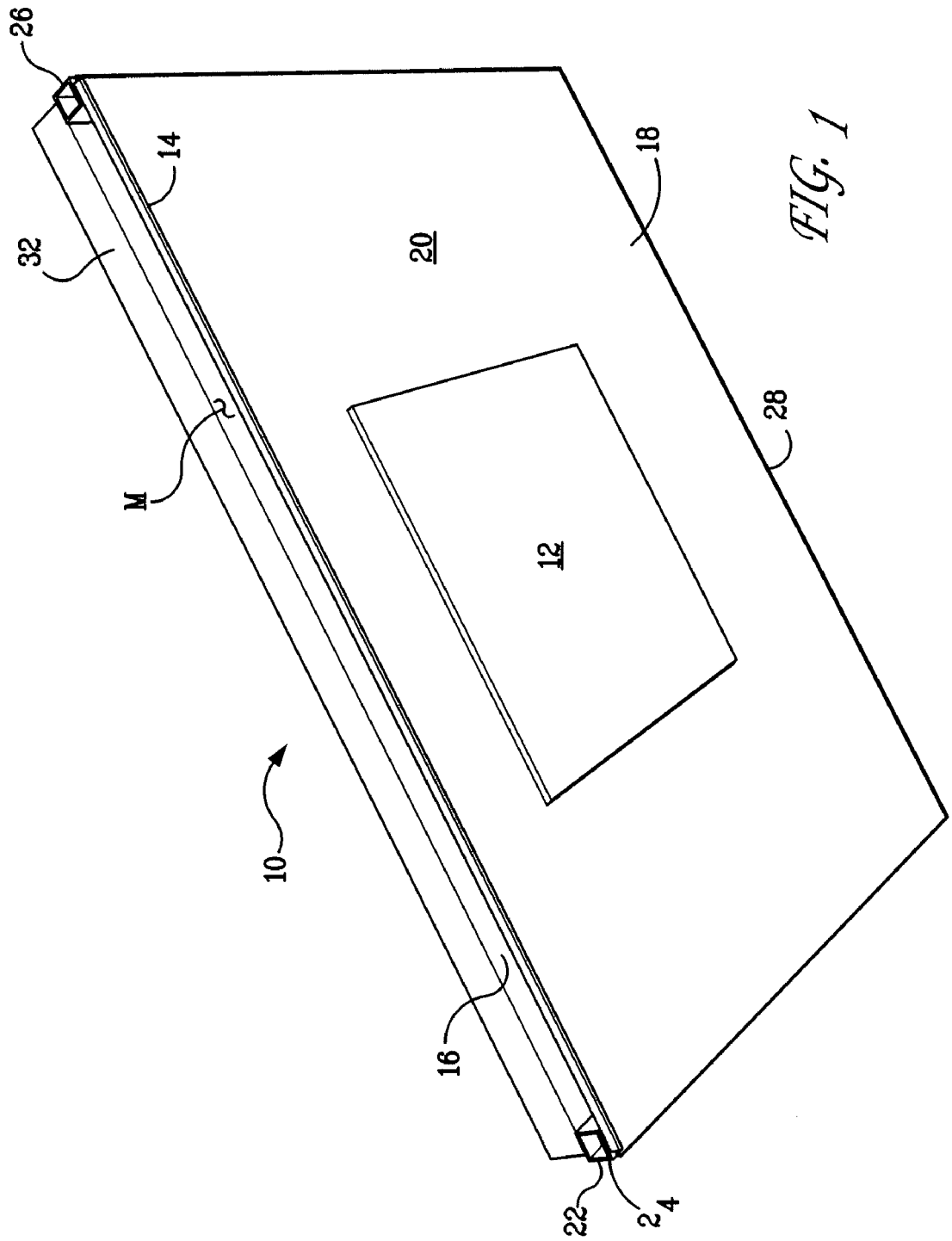
FIG. 1 shows a perspective view of a thermally conductive tank for use in an apparatus for the irradiation of a radiation sensitive material, as disclosed herein.

Unless defined otherwise, all technical and scientific terms used herein are intended to have the same meaning as is commonly understood by one of ordinary skill in the relevant art.

As used herein, the singular forms "a," "an," and "the" include the plural reference unless the context clearly dictates otherwise.

As used herein, the term "sterilize" is intended to mean a reduction in the level of at least one active or potentially active biological contaminant or pathogen found on the radiation sensitive materials being treated in accordance herewith.

As used herein, the term "biological contaminant or pathogen" is intended to mean a contaminant or pathogen that, upon direct or indirect contact with a radiation sensitive material, may have a deleterious effect upon a recipient thereof. As used herein, the term "active biological contaminant or pathogen" is intended to mean a biological contaminant or pathogen that is capable of causing a deleterious effect, either alone or in combination with another factor, such as a second biological contaminant or pathogen or a native protein or antibody, upon a recipient of the radiation sensitive material.

As used herein, the term "radiation" is intended to mean radiation of sufficient energy to sterilize at least some component of the irradiated biological material. Types of radiation include, but are not limited to, the following: (i) corpuscular (streams of subatomic particles such as neutrons, electrons, and/or protons); (ii) electromagnetic (originating in a varying electromagnetic field, such as radio waves, visible (both mono and polychromatic) and invisible light, infrared, ultraviolet radiation, x-radiation, and gamma rays and mixtures thereof); and (iii) sound and pressure waves.

Radiation is often described as either ionizing (capable of producing ions in irradiated materials) radiation, such as gamma rays, and non-ionizing radiation, such as visible light. The sources of such radiation may vary and, in general, the selection of a specific source of radiation is not critical provided that sufficient radiation is given in an appropriate time and at an appropriate rate to effect sterilization. In practice, gamma radiation is usually produced by isotopes of Cobalt or Cesium, while UV and X-rays are produced by machines that emit UV and X-radiation, respectively, and electrons are often used to sterilize materials in a method known as "E-beam" irradiation that involves their production via a machine. Visible light, both mono- and polychromatic, is produced by machines and may, in practice, be combined with invisible light, such as infrared and UV, that is produced by the same machine or a different machine.

As indicated above, ionizing radiation treatments such as gamma-irradiation, electron beam irradiation, and x-ray irradiation generate free radicals and other activated molecules that damage the biological components of contaminating bacteria, fungi, and viruses and thus ensures their inactivation. However, the biological materials, themselves, may also be damaged by free radicals and activated molecules, which can harm the integrity of the material.

Likewise, many implanted medical devices are composed of bioabsorbable materials that are more sensitive to certain physical and chemical treatments, particularly those necessary to sterilize medical devices. This is especially true of exposure of these materials to ionizing radiation such as gamma-irradiation, electron beam irradiation, and x-ray irradiation. Such treatments generate free radicals and other activated molecules that damage the biological components of contaminating bacteria, fungi, and viruses and thus ensures their inactivation. The constituent atoms of bioabsorbable materials are also damaged by free radicals and activated molecules, which reduces the structural integrity of the material.

A beneficial irradiation process is usually specified by a minimum absorbed dose to achieve the desired effect and a maximum dose limit that the product can tolerate and still be functional. The dose distribution within a product depends on process load characteristics, irradiation conditions, and operating parameters. The operating parameters consist of beam characteristics, such as electron energy and beam current, beam dispersion parameters, and product material handling. These critical parameters must be controlled to obtain reproducible results. Before a radiation facility is used, it must demonstrate its ability to deliver specified, controllable doses in a reproducible manner. This involves testing the process equipment, calibrating the equipment and dosimetry system, and characterizing the magnitude, distribution and reproducibility of the dose absorbed by a reference material.

To ensure that products are irradiated with reproducible doses, process control requires product handling procedures before, during and after the irradiation, consistent orientation of the products during irradiation, monitoring of critical process parameters, routine product dosimetry and documentation of the required activities and functions. To this end, an apparatus for the irradiation of a radiation sensitive material is disclosed herein, which serves to provide a controlled environment for conducting an irradiation process.

Referring now to FIG. 1, an apparatus 10 for the irradiation of a radiation sensitive material 12 is shown. Apparatus 10 includes at least one thermally conductive tank 14 for containing a heat transfer medium M therein, the at least one thermally conductive tank 14 having a first wall 16 and a second wall 18 in a parallel spaced relationship, the second wall 18 having an outer surface 20 for placing a radiation sensitive material 12 thereon.

Thermally conductive tank 14 of apparatus 10 also includes a perimeter frame 22 which extends about at least three sides of thermally conductive tank 14. Perimeter frame 22 may be formed from a single section of metallic stock, such as bar stock, hollow rectangular stock or solid rectangular stock or from individual sections of such materials to form the sides and bottom of thermally conductive tank 14. When formed from individual sections, perimeter frame 22 may include a pair of side frame members 24 and 26 which may be attached through the use of welding, fasteners or the like, to bottom frame member 28. Perimeter frame 22 should be constructed of radiation resistant materials. High-purity aluminum is preferred, although other materials may be employed. As may be appreciated, in constructing thermally conductive tank 14, first wall 16 and second wall 18 of thermally conductive tank 14 is in sealing engagement with perimeter frame 22, so as to form a liquid tight thermally conductive tank 14.

Thermally conductive tank 14 of apparatus 10 should be constructed of radiation resistant materials. Moreover, first wall 16 and second wall 18 of the thermally conductive tank 14 may be formed from a material having a high coefficient of thermal conductivity. Thermal conductivity, k, is the intensive property of a material that indicates its ability to conduct heat. It is defined as the quantity of heat, Q, transmitted in time, t, through a thickness, L, in a direction normal to a surface of area, A, due to a temperature difference, $\Delta T$, under steady state conditions, the heat transfer dependent only upon the temperature gradient. By high coefficient of thermal conductivity is meant a material having a coefficient of thermal conductivity of at least about 100. Suitable materials will have a coefficient of thermal conductivity of at least 100 or at least 150 or at least 200. High-purity aluminum is preferred, although other materials may be employed. In the selection of a suitable material, it is also important that walls 16 and 18 of thermally conductive tank 14 do not bend or become misshapen once they have achieved a heat transfer medium material-specific steady-state temperature. In this regard, a wall thickness of about 1.5 to about 3.0 mm has utility in the practice of the apparatus, system and method disclosed herein.

In the assembly of thermally conductive tank 14 of apparatus 10, first wall 16 and second wall 18 may be welded, such as by tack welding, to perimeter frame 22 and then sealed using a suitably radiation-resistant material. Additionally, front wall 16 of thermally conductive tank 14 may be provided with a handle member 32, which stabilizes the construction of thermally conductive tank 14, while providing a handy means to grip thermally conductive tank 14.

Thermally conductive tank 14 provides passive temperature stabilization during transport to, through and out of the radiation field. The heat transfer medium M and the design of thermally conductive tank 14 serve to provide an absorbed dose build-up required to produce a uniform dose profile over a large volume during the irradiation process. As will be explained in more detail hereinbelow, one, two or more thermally conductive tanks may be used in the irradiation treatment procedures disclosed herein.

In one form, a securement plate (not shown) having a first surface and a second surface, the second surface for contacting the radiation sensitive material 12, may be employed to cover radiation sensitive material 12 and form a system for the irradiation of radiation sensitive material 12. A means for securing the securement plate to thermally conductive tank 14 so that the second surface of the securement plate faces the outer surface 20 of second wall 18 of the thermally conductive tank 14 when the radiation sensitive material 12 is placed therebetween, when the securement plate is employed. The means for securing the securement plate to thermally conductive tank 14 can include at least one clamp (not shown).

Figure 2:
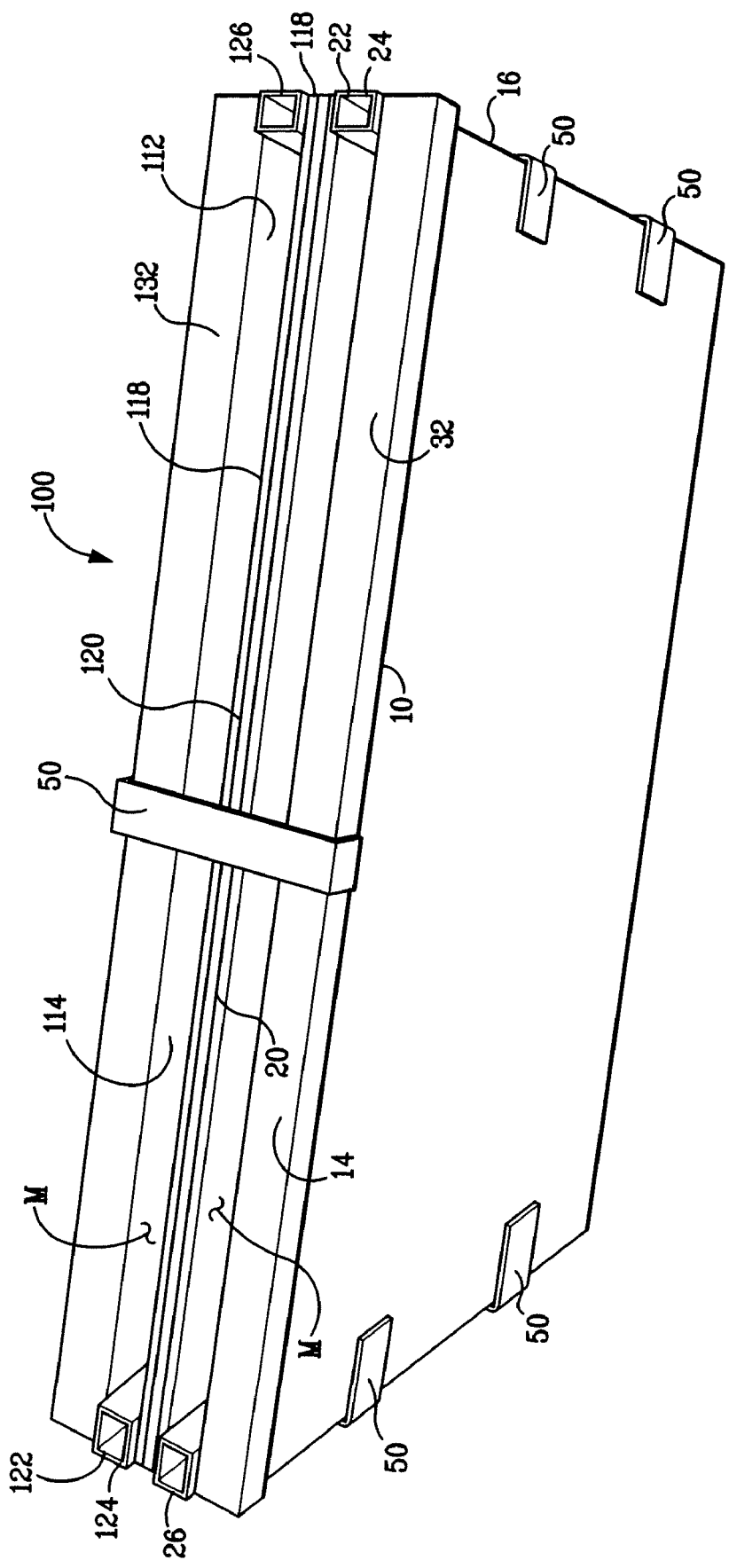
FIG. 2 shows a system for the irradiation of a radiation sensitive material having a pair of thermally conductive tanks secured with clamps for holding a radiation sensitive material.

Referring now to FIG. 2, a system 100 for the irradiation of a radiation sensitive material is shown. The system 100 includes first thermally conductive tank 14 for containing a heat transfer medium M therein, as shown in FIG. 1. As indicated above, first thermally conductive tank 14 has a first wall 16 and a second wall 18 in a parallel spaced relationship, the second wall 18 having an outer surface 20 for placing a radiation sensitive material 12 thereon. System 100 includes a second thermally conductive tank 114 for containing a heat transfer medium M therein, the second thermally conductive tank 114 having a first wall 116 and a second wall 118 in a parallel spaced relationship, the second wall 118 having an outer surface 120 for contacting the radiation sensitive material 12 and means for securing the second thermally conductive tank 114 to the first thermally conductive tank 14 to form assembly 100 so that the outer surface 120 of the second wall 118 of the second thermally conductive tank 114 faces the outer surface 20 of the second wall 18 of the first thermally conductive tank 14 when the radiation sensitive material 12 is placed therebetween.

Thermally conductive tank 114 of system 100 also includes a perimeter frame 122 which extends about at least three sides of thermally conductive tank 114. Perimeter frame 122 may be formed from a single section of metallic stock, such as bar stock, hollow rectangular stock or solid rectangular stock or from individual sections of such materials to form the sides and bottom of thermally conductive tank 114. When formed from individual sections, perimeter frame 122 may include a pair of side frame members 124 and 126 which may be attached through the use of welding, fasteners or the like, to bottom frame member 128. Perimeter frame 122 should be constructed of radiation resistant materials. High-purity aluminum, again, is preferred, although other materials may be employed. As may be appreciated, in constructing thermally conductive tank 114, first wall 116 and second wall 118 of thermally conductive tank 114 is in sealing engagement with perimeter frame 122, so as to form a liquid tight thermally conductive tank 114.

Thermally conductive tank 114 of system 100 should be constructed of radiation resistant materials. Moreover, first wall 116 and second wall 118 of the thermally conductive tank 114 may be formed from a material having a high coefficient of thermal conductivity. By high coefficient of thermal conductivity is meant a material having a coefficient of thermal conductivity of at least about 100. Suitable materials will have a coefficient of thermal conductivity of at least 100 or at least 150 or at least 200. High-purity aluminum is preferred, although other materials may be employed. In the selection of a suitable material, it is also important that walls 116 and 118 of thermally conductive tank 114 do not bend or become misshapen once they have achieved a heat transfer medium material-specific steady-state temperature. In this regard, a wall thickness of about 1.5 to about 3.0 mm has utility in the practice of the apparatus, system and method disclosed herein.

In the assembly of thermally conductive tank 114 of system 100, first wall 116 and second wall 118 may be welded, such as by tack welding, to perimeter frame 122 and then sealed using a suitably radiation-resistant material. Additionally, front wall 116 of thermally conductive tank 114 may be provided with a handle member 132, which stabilizes the construction of thermally conductive tank 114, while providing a handy means to grip thermally conductive tank 114.

Figure 3:
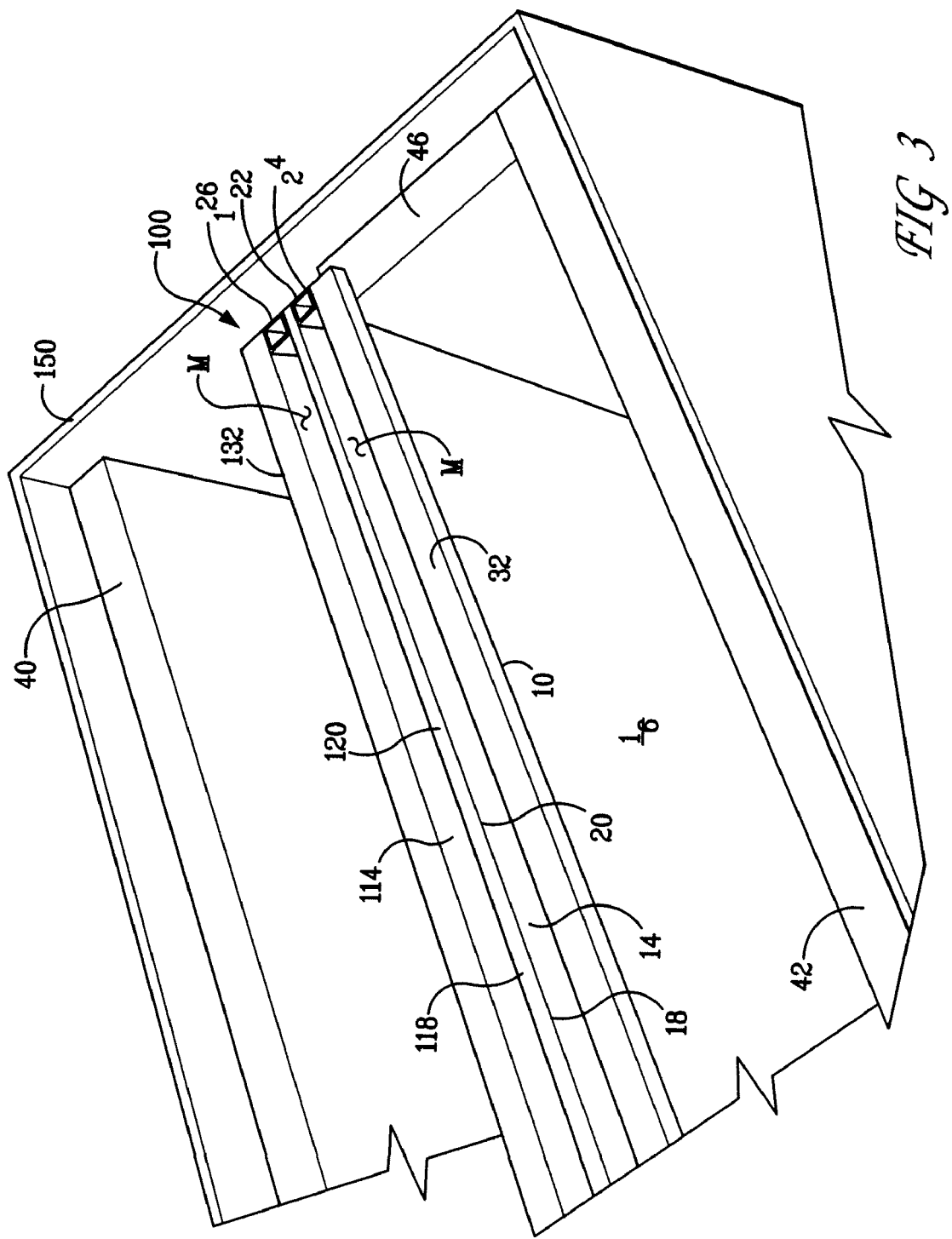
FIG. 3 shows an assembly for the irradiation of a radiation sensitive material that employs the system of FIG. 2.

In use, thermally conductive tanks 14 and 114 of assembly 100 are secured through the use of means for securing the second thermally conductive tank 114 to first thermally conductive tank 14. As shown in FIG. 3, the outer surface 120 of second wall 118 of second thermally conductive tank 114 faces outer surface 20 of second wall 18 of first thermally conductive tank 14 with radiation sensitive material 12 placed therebetween. The securing means of assembly 100 may be a set of clamps 50, as shown, a metal band (not shown), which fully surrounds thermally conductive tanks 14 and 114 of assembly 100, an elastic band or other resilient band (not shown), which fully surrounds thermally conductive tanks 14 and 114 of assembly 100, common fasteners (not shown), or the like. The means for securing second thermally conductive tank 114 to first thermally conductive tank 14 may include at least one clamp 50.

Generally, the thickness of the radiation sensitive material 12 to be irradiated within the assembly 100 is about one centimeter, although as may be appreciated by those skilled in the art, the thickness of the radiation sensitive material 12 may vary. The surface area of the first wall 16 and second wall 18 of the first thermally conductive tank 14 and the first wall 116 and second wall 118 of the second thermally conductive tank 114 should be, within known irradiation material transport system limitations, as large as possible in order to provide maximum space for the samples to be irradiated.

Referring now to FIG. 3, prior to irradiation, system 100 is placed into a container 150, such as a cardboard box or other container appropriate for application in the radiation process. As may be appreciated, container 150 is sized to enable the container 150 to easily fit within the radiation facility's material transport system (not shown). Container 150 can be optimized for maximum product area and/or volume movement through the radiation material transport system.

Foamed thermoplastic slabs 40 and 42 may be placed in parallel with first wall 16 and second wall 18 of first thermally conductive tank 14 and first wall 116 and second wall 118 of second thermally conductive tank 114, on either side of assembly 100 and within container 150. Additionally, foamed thermoplastic slabs 44 and 46 may also be placed perpendicularly to first wall 16 and second wall 18 of first thermally conductive tank 14 and first wall 116 and second wall 118 of second thermally conductive tank 114, within container 150. Foamed thermoplastic slabs 40, 42, 44, 46 and 48 may be formed from polyethylene foam, such as Ethafoam™ polyethylene foam, available from The Dow Chemical Company of Midland, Mich. As may be appreciated, foamed thermoplastic slabs 40, 42, 44, 46 and 48 assist in providing dose build-up and aid in improving the dose uniformity while also providing structural support.

The thermally conductive tanks 14 and 114 may be used for irradiation with an electron accelerator (e-beam) having accelerator electron kinetic energies in the range of about 8 to about 12 MeV. As may be appreciated by those skilled in the art, thermally conductive tank 14 has utility in the practice of ISO/ASTM 51649, the contents of which are hereby incorporated by reference for all that they disclose. The apparatus, system and methods disclosed are useful in the practice of Monte Carlo simulations of mixed electron kinetic energy spectra. There are, of course, no known restrictions regarding the type of electron accelerator with which the apparatus, system and methods disclosed may be used.

The absorbed dose homogeneity, that is, the ratio of absorbed dose maximum (Dmax) to absorbed dose minimum (Dmin), measured over the irradiation area of interest of the radiation sensitive material 12 is expected to be:

Dmax/Dmin<1.12

Referring again to FIG. 1, thermally conductive tank 14 has the ability to provide passive cooling or warming capabilities. The available temperature range, for selected single target passive steady-state temperatures, is about −60° C. to 80° C. When dry ice is used as the heat transfer medium M, a steady-state irradiation temperature of about −75° C. may be achieved. When using chilled solid water ice as heat transfer medium M, a steady-state irradiation temperature of about −10° C. may be achieved. When using crushed solid water ice as heat transfer medium M, a steady-state irradiation temperature of about 0° C. may be achieved. When using liquid water, or polypropylene bead filler material or polystyrene beads as heat transfer medium M, steady-state irradiation temperatures of about 22° C. may be achieved. As may be appreciated, this would be approximately equivalent to operation at laboratory ambient temperatures. When using heated liquid water, heated polypropylene beads, heated polyethylene beads or heated polystyrene beads as heat transfer medium M, a steady-state irradiation temperature of about 45° C. may be achieved.

Other heat transfer medium strategies are possible. These may include, but are not limited to, other chilled fluids, chilled solids, heated fluids or heated solids. In all cases, the heat transfer medium must be able to be placed within the first wall 16 and a second wall 18 of an empty thermally conductive tank 14.

In operation, the target steady-state temperature of the radiation sensitive material 12 should be achieved in a short time period, generally less than 25 minutes, when placed in physical contact within assembly 100, each maintained at equivalent steady-state temperatures. The target steady-state temperature of the radiation sensitive material 12 should then be maintained for a period of not less than about 20 minutes after reaching steady-state temperature, as described hereinabove. The target steady-state temperature of the radiation sensitive material 12 should be that of the assembly 100 at the time of irradiation.

As may be appreciated, thermally conductive tanks 14 and 114 of system 100 form a passive temperature controlling and stabilization system. In operation, near-instantaneous heating of the radiation sensitive material 12 will occur during the irradiation process. Following this near-instantaneous heating of radiation sensitive material 12, cooling to the steady-state temperature of the thermally conductive tanks 14 and 114 of system 100 will generally occur. The magnitude of the near-instantaneous heating of the radiation sensitive material 12 during the irradiation process will be directly related to the applied absorbed dose and the effective heat capacity (specific heat) of the radiation sensitive material 12.

The thermally conductive tanks 14 and 114 of system 100 are capable of holding and retaining fluids, which are used as the heat transfer medium, during the irradiation process. The thermally conductive tanks 14 and 114 of system 100 are constructed of radiation resistant materials. As indicated hereinabove, high-purity aluminum is particularly preferred, although other materials may be employed. In the selection of a suitable material, it is important that walls 16 and 18 of thermally conductive tank 14 and walls 116 and 118 of second thermally conductive tank 114 do not bend or become misshapen once they have achieved a heat transfer medium material-specific steady-state temperature. In this regard, a wall thickness of about 1.5 to about 3.0 mm has utility in the practice of the present invention.

In another form, a method of irradiating a radiation sensitive material having a first surface and a second surface is herein disclosed. The method includes the steps of placing the first surface of a radiation sensitive material on a first thermally conductive tank for containing a heat transfer medium therein, the first thermally conductive tank having a first wall and a second wall in a parallel spaced relationship, the second wall having an outer surface for receiving the radiation sensitive material, placing a second thermally conductive tank for containing a heat transfer medium therein upon the second surface of a radiation sensitive material radiation sensitive material, the second thermally conductive tank having a first wall and a second wall in a parallel spaced relationship, the second wall having an outer surface for contacting the radiation sensitive material, securing the second thermally conductive tank to the first thermally conductive tank to form an assembly so that the outer surface of the second wall of the second thermally conductive tank faces the outer surface of the second wall of the at least one thermally conductive tank when the radiation sensitive material is placed therebetween, filling each of the first and the second thermally conductive tanks with a heat transfer medium and irradiating the radiation sensitive material with a suitable radiation at an effective rate and time to sterilize the radiation sensitive material.

The radiation employed in the method disclosed herein may be any radiation effective for the sterilization of the radiation sensitive material being treated. The radiation may be corpuscular, including accelerated electron irradiation (E-beam) radiation. The radiation may be gamma radiation from a cobalt or other isotopic source or irradiation with X-rays.

According to the method disclosed herein, the radiation sensitive material is irradiated with the radiation at a rate and/or dose effective for the sterilization of the radiation sensitive material, while not producing an unacceptable level of damage to that material. Suitable rates of irradiation may vary depending upon the nature and characteristics of the particular radiation sensitive material being irradiated, the particular form of radiation involved and/or the particular biological contaminants or pathogens being inactivated. Suitable rates of irradiation can be determined empirically by one skilled in the art. The rate and/or dose of irradiation may be constant for the duration of the sterilization procedure. When this is impractical or otherwise not desired, a variable or discontinuous irradiation may be utilized.

According to the method disclosed herein, the rate and/or dose of irradiation may be optimized to produce the most advantageous combination of product recovery and time required to complete the operation. The rate and/or dose of irradiation are selected to minimize structural damage to the bioabsorbable polymeric material while still sterilizing the bioabsorbable polymeric material.

According to the method disclosed herein, the radiation sensitive material to be sterilized is irradiated with the radiation for a time effective for the sterilization of the radiation sensitive material. Combined with irradiation rate, the appropriate irradiation time results in the appropriate dose of irradiation being applied to the radiation sensitive material. Suitable irradiation times may vary depending upon the particular form and rate of radiation involved and/or the nature and characteristics of the particular bioabsorbable polymeric material being irradiated. As may be appreciated, suitable irradiation times can be determined empirically by one skilled in the art.

The method disclosed herein is effective against such biological contaminants or pathogens, including the various viruses, bacteria (including inter- and intracellular bacteria, such as mycoplasmas, ureaplasmas, nanobacteria, chlamydia, rickettsias), yeasts, molds, fungi, prions or similar agents responsible, alone or in combination, for TSEs and/or single or multicellular parasites known to those of skill in the art. Examples of biological contaminants or pathogens include, but are not limited to, the following: viruses, such as human immunodeficiency viruses and other retroviruses, herpes viruses, filoviruses, circoviruses, paramyxoviruses, cytomegaloviruses, hepatitis viruses (including hepatitis A, B and C and variants thereof), pox viruses, toga viruses, Epstein-Barr viruses and parvoviruses; bacteria (including mycoplasmas, ureaplasmas, nanobacteria, chlamydia, rickettsias), such as *Escherichia, Bacillus, Campylobacter, Streptococcus* and *Staphylococcus*; parasites, such as Trypanosoma and malarial parasites, including Plasmodium species; yeasts; molds; and prions, or similar agents, responsible alone or in combination for TSE (transmissible spongiform encephalopathies), such as scrapie, kuru, BSE (bovine spongiform encephalopathy), CJD (Creutzfeldt-Jakob disease), Gerstmann-Straeussler-Scheinkler syndrome, and fatal familial insomnia.

Specific embodiments of the present invention will now be described further, by way of example. While the following examples demonstrate certain embodiments of the invention, they are not to be interpreted as limiting the scope of the invention, but rather as contributing to a complete description of the invention.

Example

A penetration budget for a system as depicted in FIG. 3 and described herein, is shown below.

TABLE 1

PENETRATION BUDGET

| Element No. | Material | Thickness (cm) | Density (g/cm$^3$) | z (g/cm$^2$) |
|---|---|---|---|---|
| 150 of FIG. 3 | Cardboard Box | 0.5 | 0.1 | 0.05 |
| 42 of FIG. 3 | Ethafoam ™ | 5.0 | 0.1 | 0.5 |
| 16 of FIG. 3 | Aluminum Wall | 0.2 | 2.7 | 0.54 |
| M of FIG. 3 | Water | 2.0 | 1.0 | 2.0 |
| 18 of FIG. 3 | Aluminum Wall | 0.2 | 2.7 | 0.54 |
| 12 (See FIG. 1) | Product | 1.0 | 0.15 | 0.15 |
| | TOTAL | | | 3.78 |

Tests were conducted using the system as depicted in FIG. 3 and described above to demonstrate the cooling ability of a set of thermally conductive tanks 14 and 114 filled with pelletized dry ice (solid $CO_2$), when applied to a target material (product). The tests were performed in substantial accordance with ISO/ASTM 516492005(E), Standard Practice for Dosimetry in an Electron Beam Facility for Radiation Processing at Energies Between 300 keV and 25 MeV1.

Figure 4:
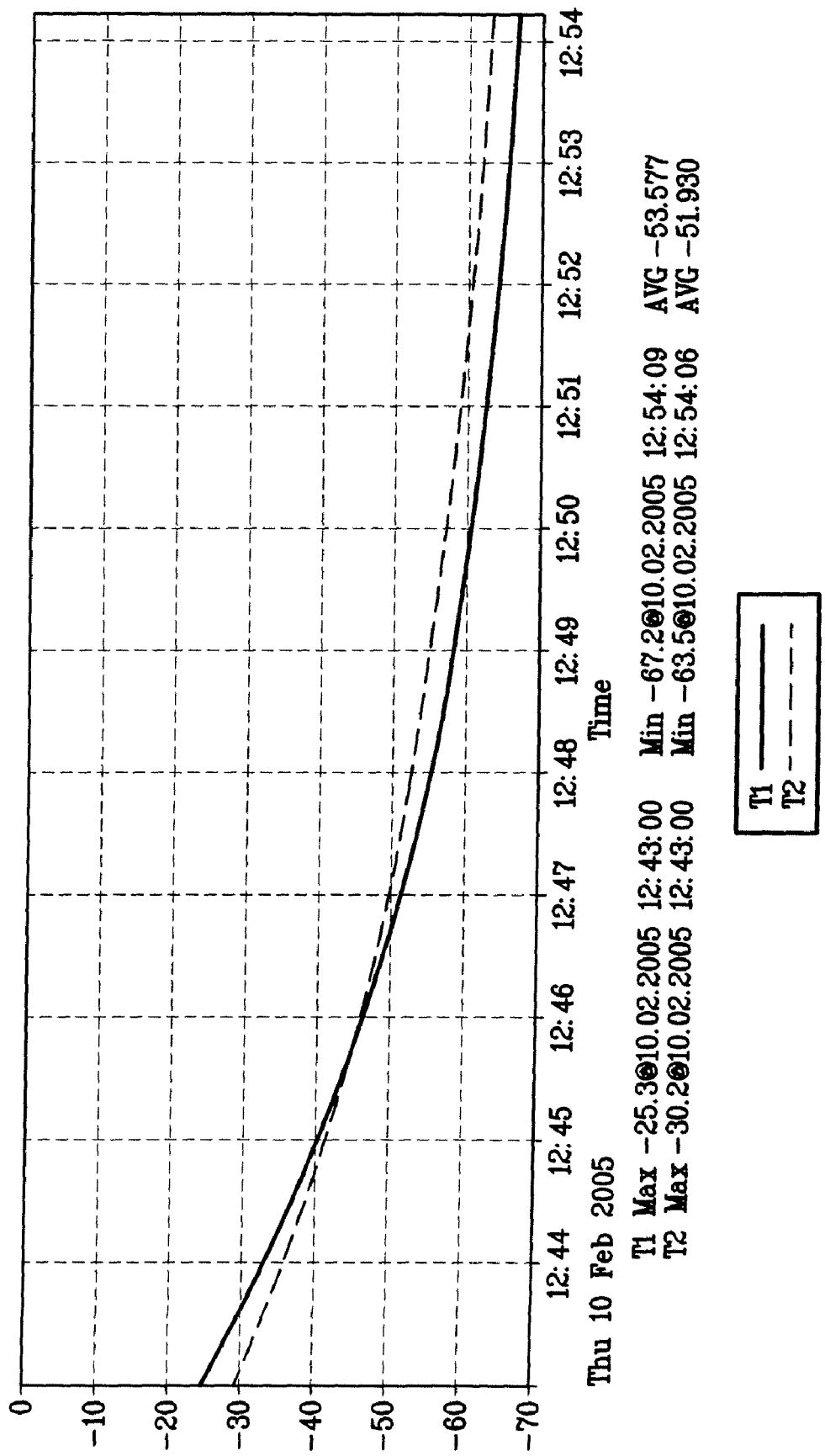
FIG. 4 presents a temperature distribution at two locations of a radiation sensitive material using a thermally conductive tank filled with pelletized dry ice.

FIG. 4 shows the temperature distribution within 2 locations of the target material (product), measured using thermocouples, after filling the tank with pelletized dry ice. Within approximately 20 minutes the target temperature of <−70° C. was achieved.

Dose distribution data were also obtained and are presented in Table 2, below.

TABLE 2

DOSE DISTRIBUTION DATA
(Doses in kGy)

| 10.0 | 10.1 | 10.0 | 9.5  | 9.4  | 10.1 | 9.4  | 10.0 | 9.7 | 9.7  | 9.7  |
|------|------|------|------|------|------|------|------|-----|------|------|
| 9.8  | 10.0 | 10.0 | 9.8  | 9.5  | 9.9  | 9.7  | 9.8  | 9.8 | 10.1 | 10.2 |
| 10.0 | 9.8  | 9.8  | 9.8  | 9.7  | 9.6  | 9.6  | 9.8  | 9.7 | 9.8  | 10.1 |
| 10.4 | 10.1 | 9.8  | 9.9  | 9.4  | 9.6  | 9.7  | 9.8  | 9.6 | 9.7  | 9.9  |
| 9.7  | 9.9  | 9.7  | 9.8  | 9.9  | 9.9  | 9.8  | 9.8  | 9.7 | 9.8  | 9.9  |
| 10.0 | 9.8  | 10.2 | 9.8  | 9.9  | 9.8  | 9.8  | 9.8  | 9.8 | 9.6  | 9.9  |
| 10.1 | 10.1 | 10.3 | 10.3 | 10.1 | 10.2 | 10.2 | 10.2 | 9.9 | 10.0 | 9.7  |

As may be seen from a review of the data of Table 2, the value for absorbed dose maximum (Dmax) was 10.4, while the value of absorbed dose minimum (Dmin) was 9.4.

While the subject invention has been illustrated and described in detail in the drawings and foregoing description, the disclosed embodiments are illustrative and not restrictive in character. All changes and modifications that come within the scope of the invention are desired to be protected.

What is claimed is:

1. An apparatus for the irradiation of a radiation sensitive material, the apparatus comprising: at least one thermally conductive tank for containing a heat transfer medium therein, said at least one thermally conductive tank having a first wall and a second wall in a parallel spaced relationship, said second wall having an outer surface and a securement plate for placing a radiation sensitive material thereon, wherein said first wall and said second wall of said at least one thermally conductive tank are in sealing engagement therewith on only three sides.

2. The apparatus of claim 1, further comprising a second thermally conductive tank for containing a heat transfer medium therein, said second thermally conductive tank having a first wall and a second wall in a parallel spaced relationship, said second wall having an outer surface for contacting the radiation sensitive material.

3. The apparatus of claim 2, further comprising means for securing said second thermally conductive tank to said at least one thermally conductive tank so that said outer surface of said second wall of said second thermally conductive tank faces said outer surface of said second wall of said at least one thermally conductive tank when the radiation sensitive material is placed therebetween.

4. The apparatus of claim 3, wherein said means for securing said second thermally conductive tank to said at least one thermally conductive tank comprises at least one clamp.

5. The apparatus of claim 1, wherein said at least one thermally conductive tank further includes a perimeter frame about only three sides thereof.

6. The apparatus of claim 1, wherein said first wall and said second wall of said at least one thermally conductive tank are formed from a material having a coefficient of thermal conductivity of at least about 100.

7. The apparatus of claim 1, wherein said first wall and said second wall of said at least one thermally conductive tank are formed from high purity aluminum.

8. The apparatus of claim 1, wherein said securement plate has a first surface and a second surface, said second surface for contacting the radiation sensitive material.

9. The apparatus of claim 8, further comprising means for securing said securement plate to said at least one thermally conductive tank so that said second surface of said securement plate faces said outer surface of said second wall of said at least one thermally conductive tank when the radiation sensitive material is placed therebetween.

10. The apparatus of claim 9, wherein said means for securing said securement plate to said at least one thermally conductive tank comprises at least one clamp.

11. The apparatus of claim 1, wherein said securement plate is formed from aluminum.

12. A system for the irradiation of a radiation sensitive material, the system comprising:
   (a) a first thermally conductive tank for containing a heat transfer medium therein, said first thermally conductive tank having a first wall and a second wall in a parallel spaced relationship, said second wall having an outer surface for placing a radiation sensitive material thereon, wherein said first wall and said second wall of said at least one thermally conductive tank are in sealing engagement therewith on only three sides;
   (b) a second thermally conductive tank for containing a heat transfer medium therein, said second thermally conductive tank having a first wall and a second wall in a parallel spaced relationship, said second wall having an outer surface for contacting the radiation sensitive material; and
   (c) at least one clamp for securing said second thermally conductive tank to said first thermally conductive tank to form an assembly so that said outer surface of said second wall of said second thermally conductive tank faces said outer surface of said second wall of said at least one thermally conductive tank when the radiation sensitive material is placed therebetween.

13. The system of claim 12, further comprising a container for placing said assembly within.

14. The system of claim 13, further comprising a pair of foamed thermoplastic slabs, said pair of foamed thermoplastic slabs places on either side of said assembly and within said container.

15. The system of claim 14, wherein said pair of foamed thermoplastic slabs are formed from polyethylene foam.

16. A method of irradiating a radiation sensitive material having a first surface and a second surface, comprising the steps of:

(a) placing the first surface of a radiation sensitive material on a first thermally conductive tank for containing a heat transfer medium therein, the first thermally conductive tank having a first wall and a second wall in a parallel spaced relationship, the second wall having an outer surface for receiving the radiation sensitive material, wherein said first wall and said second wall of said at least one thermally conductive tank are in sealing engagement therewith on only three sides;

(b) placing a second thermally conductive tank for containing a heat transfer medium therein upon the second surface of a radiation sensitive material, the second thermally conductive tank having a first wall and a second wall in a parallel spaced relationship, the second wall having an outer surface for contacting the radiation sensitive material;

(c) securing the second thermally conductive tank to the first thermally conductive tank to form an assembly so that the outer surface of the second wall of the second thermally conductive tank faces the outer surface of the second wall of the at least one thermally conductive tank when the radiation sensitive material is placed therebetween;

(d) filling each of the first and the second thermally conductive tanks with a heat transfer medium; and (e) irradiating the radiation sensitive material with a suitable radiation at an effective rate and time to sterilize the radiation sensitive material.

17. The method of claim 16, wherein the radiation is gamma radiation.

18. The method of claim 16, wherein the radiation is E-beam radiation.

19. The method of claim 16, wherein the radiation is x-ray radiation.

* * * * *